United States Patent [19]

Lubock et al.

[11] Patent Number: 4,679,556
[45] Date of Patent: Jul. 14, 1987

[54] RELEASABLE HOLDER AND METHOD OF USE

[75] Inventors: Paul Lubock, Laguna Hills; Mike Sullivan, San Clemente, both of Calif.

[73] Assignee: Shiley Inc., Irvine, Calif.

[21] Appl. No.: 852,699

[22] Filed: Apr. 16, 1986

[51] Int. Cl.$^4$ .............................................. A61B 17/00
[52] U.S. Cl. ................................ 128/303 R; 128/321; 294/94; 294/19.1
[58] Field of Search .................. 128/303 R, 345, 321; 294/94, 33, 99.1, 19.1

[56] References Cited

U.S. PATENT DOCUMENTS

| | | |
|---|---|---|
| 3,409,013 | 11/1968 | Berry . |
| 3,628,535 | 12/1971 | Ostrowsky et al. . |
| 3,824,629 | 7/1974 | Shiley . |
| 3,828,787 | 8/1974 | Anderson et al. . |
| 3,860,005 | 1/1975 | Anderson et al. . |
| 4,182,446 | 1/1980 | Penny . |
| 4,211,325 | 7/1980 | Wright . |
| 4,574,800 | 3/1986 | Peers-Trevarton ............. 128/303 R |

FOREIGN PATENT DOCUMENTS 207339 2/1968 U.S.S.R. .......................... 128/303 R

OTHER PUBLICATIONS

"A suture Holder and Separator Attachment to the Starr-Edwards Prosthetic Valve Holders", Grismer et al., *Surgery, Gynecology & Obstetrigs*, Mar. 1965, pp. 583-584.

*Primary Examiner*—Michael H. Thaler
*Attorney, Agent, or Firm*—P. C. Richardson; M. Dryer; R. C. Turner

[57] ABSTRACT

A device for releasably holding an object, particularly a prosthetic heart valve, comprising a handle member integral with a key member which releasably engages a holder member having an interacting engaging screw which controls and limits the movement of integral cooperating fingers for holding and releasing said object; and a package assembly for storing under sterile conditions a holder member of said device attached to a prosthetic heart valve comprising a clam shell mechanism for releasably holding said holder member and valve.

7 Claims, 14 Drawing Figures

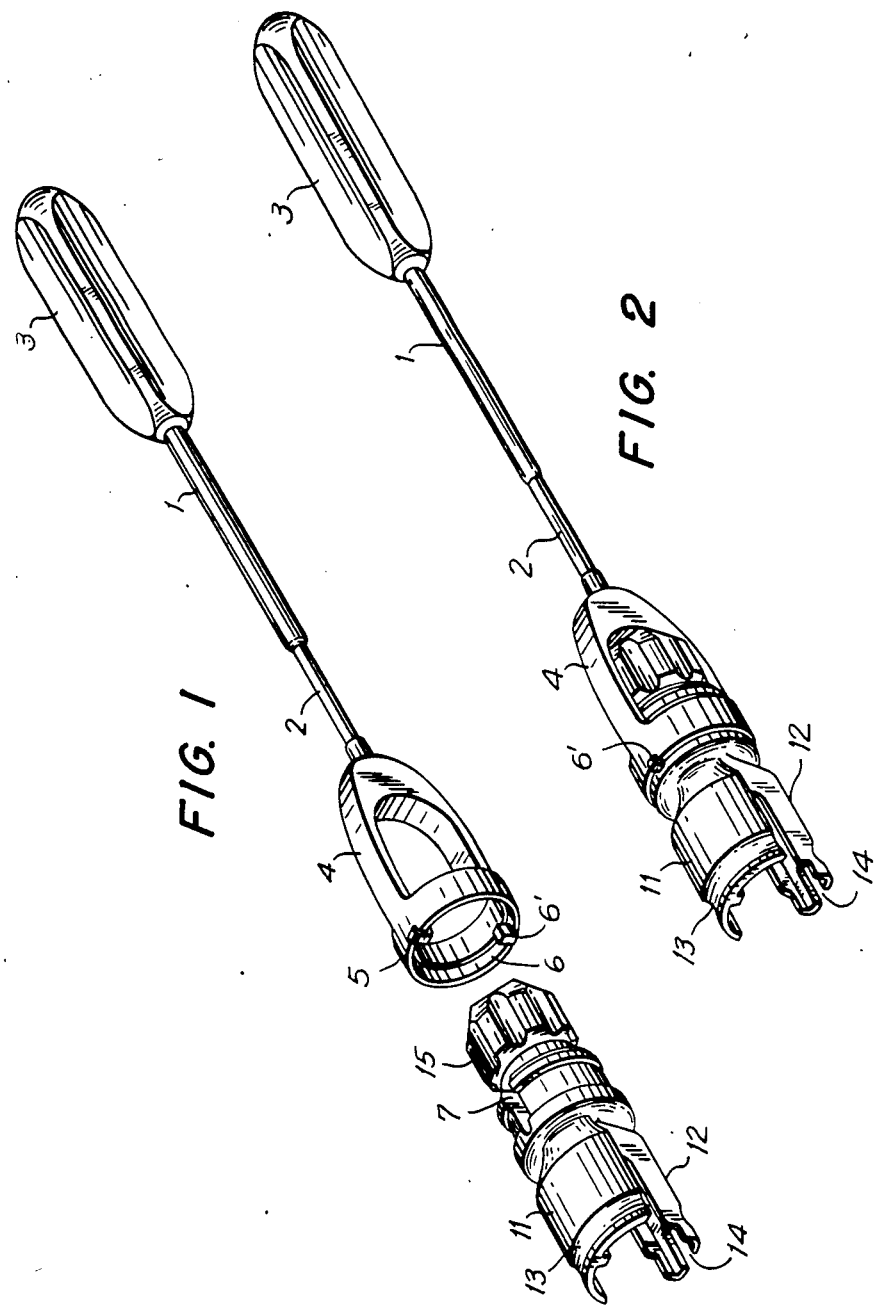

RELEASABLE HOLDER AND METHOD OF USE

BACKGROUND OF THE INVENTION

This invention relates to a device for releasably holding an object and is particularly concerned with a holder for releasably holding a heart valve. The invention also relates to a container assembly for packaging a heart valve and holder member.

Various types of heart valve prostheses are known in the art. One example of a heart valve prosthesis is the pivoted discoid heart valve disclosed in U.S. Pat. No. 3,824,629. To facilitate the implantation of this type of prosthesis, instruments which releasably hold the valve also have been proposed in the art.

One such instrument is disclosed in U.S. Pat. No. 3,409,013. This instrument comprises a shank, a plurality of jaws having outwardly directed hooks at their distal ends and being pivotally movable about the shank. The instrument also includes a slidable suture retaining device mounted on the shank.

A disposable collet for holding a pivoting disc heart valve is disclosed in U.S. Pat. Nos. 3,828,787 and 3,860,005. Said collet has an enlarged head and an elongated flexible band integral therewith. The band is adapted to be positioned over the side arms and disc of the valve to cover the side arms and disc.

U.S. Pat. No. 3,628,535 discloses a valve insertion unit for holding a heart valve to be inserted within the body. The unit includes an expansible retaining ring, receiving means and spreading means for positioning and holding the heart valve.

Devices are also known for retaining artificial heart valves during storage and examples of such holders are disclosed in U.S. Pat. Nos. 4,182,446 and 4,211,325. A surgical method of using a sterile packaged prosthesis is disclosed in U.S. Pat. No. 4,065,816.

Copending patent application Ser. No. 468,561, now U.S. Pat. No. 4,585,453, describes and claims a disposable, single-piece holder having arms that are prepositioned on the valve body.

SUMMARY OF THE INVENTION

The present invention relates to a novel valve holder assembly comprising a holder head and handle which operate advantageously in combination to:

(a) minimize possible valve damage during implantation;
(b) simplify presentation to the surgical field; and
(c) reduce time for valve replacement.

In accordance with the invention there is provided a device for releasably holding an object which comprises:

an elongated rod having a proximal end and a distal end, said rod being attached at its proximal end to a handle and at its distal end to a bifurcated member terminating in a ring enclosing a resilient circular key member, a holder member terminating in at least two cooperating fingers and having a cylindrical head with an axial screw thread, said fingers being adapted to engage with and grip an object to be held and said cylindrical head being adapted to be locked through a snapping engagement, within said resilient key member, and an engaging screw located in said screw thread and adapted to interact with said holder member so as to control and limit the movement of said fingers and thereby upon turning, to engage and disengage said fingers with respect to a desired object.

A preferred embodiment of the invention is a device, as described above, in which said fingers are adapted to engage with and grip an annular heart valve ring from the inside and gripping is achieved by turning the engaging screw to expand the fingers outwardly.

The invention also provides a package assembly for storing under sterile conditions a holder member of a device as described above in engagement with a prosthetic heart valve, which assembly comprises an outer container and an inner container, said outer container comprising a bottom portion and a tight fitting lid, and said inner container comprising a housing having a cover, said housing being defined by one or more vertical walls having two pairs of slots diametrically facing each other, each pair of slots carrying a double pivoting fastener adapted to slide up and down within said slots, each fastener being snap fitted to a downwardly extending limb attached to a split platform having a central hole, the combination of split platform, limbs, pivoting fasteners and associated slots forming a clam shell mechanism adapted to accommodate said holder member and attached heart valve for storage and shipment and to release same after engagement of a cooperating key member with said holder member.

In a preferred embodiment of the above-described package assembly said housing has a cylindrical wall and a circular flat base.

DETAILED DESCRIPTION OF THE INVENTION

Although a device according to the invention is capable of releasably holding any object of appropriate shape and dimensions adapted to be engaged and released by the fingers of said holder member, the preferred device has been particularly designed for releasably holding a prosthetic heart valve, especially a valve of the pivoting disc type, and the following detailed description is directed primarily to this preferred embodiment.

In such an embodiment preferably there are two fingers, each having the configuration of an arc of a circle and each being diametrically opposed to the other and each being provided with a shallow indent on the outer side near its distal end to accommodate the valve ring and prevent slipping when the engaging screw is tightened.

It is clear, since it is important to maintain strict sterile conditions during any surgical operation, that all the parts of said device should be made from sterilizable materials. A particularly suitable and preferred material for the elongated rod and key member of the device is stainless steel, especially since it is desirable, for the purpose of manipulation when necessary, that a portion of said elongated rod near its distal end is flexible. Preferably the remaining parts of the device are made from substantially rigid plastics material, for example, ultra high molecular weight polyethylene, the acetal resin commercial available under the Trademark "Delrin", polypropylene or polyfluoroethylene. The preferred plastic for forming the handle member and engaging screw is "Delrin".

The preferred embodiment described above is particularly suitable for releasable holding a prosthetic heart valve and, accordingly, the invention further provides a method for releasable holding a prosthetic heart valve to facilitate placement or replacement thereof which comprises engaging the annular ring of said heart valve between the fingers of said device, turning the engaging screw of said device to expand said fingers and thereby grip and hold said heart valve.

DESCRIPTION OF THE DRAWINGS

A preferred embodiment of the invention is illustrated in the accompanying drawings, in which:

FIG. 1 is a perspective view of the device showing the integral handle, elongated rod and bifurcated member separated from the holder member;

FIG. 2 is a perspective view of the device of FIG. 1 showing the members locked together;

Referring the drawings, FIGS. 1, 2 and 3 illustrate a device according to the invention comprising an elongated rod 1, preferably in the form of a stainless steel cylindrical shaft having a flexible portion 2 near its distal end. The object of this flexible portion is to enable the surgeon to easily bend the shaft, if necessary, to manipulate the positioning of the valve. Attached to the proximal end of the shaft is a handle 3, preferably fluted as illustrated for easy grip and preferably made from a substantially rigid plastic such as "Delrin".

Figure 3:
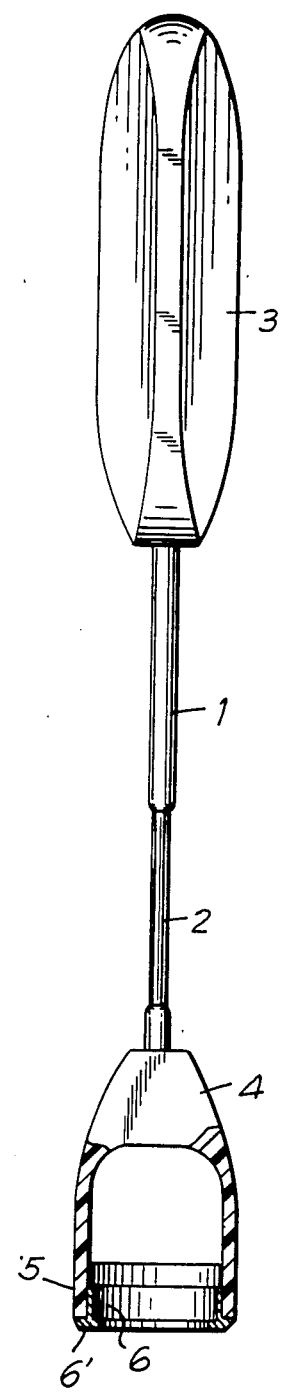
FIG. 3 is a side elevation, partly in cross-section of the integral handle, elongated rod and bifurcated member.

The distal end of the shaft is integrally attached to a bifurcated member 4, preferably made from the same plastic as the handle, e.g. "Delrin". The bifurcated member terminates in a ring 5 which encloses a resilient circular key member 6. This key member is preferably a stainless steel ring having a pair of diametrically opposed projecting tabs, 6', 6'.

The key tabs are adapted to fit into slots 7 in the outer wall of a holder member 8 having a cylindrical head 9 with a projecting lip around its upper periphery, so that the key member 6 snap fits over said lip. The cylindrical head had an axial screw thread 10 (see FIG. 6). The distal end of the holder member is in the form of two cooperating fingers 11, 12. In the embodiment illustrated, the fingers have a configuration adapted to hold a monostrut valve (aortic or mitral). Thus the finger 11 is a solid extending element having an arcuate cross-section, the curvature of the arc being in conformity with the curvature of the ring of the valve for which the device is to be used. The finger has a narrow groove 13 around its outside surface near its distal end (see FIGS. 5 and 6). This groove accommodates the ring of the heart valve when the latter is held in the device and prevents slippage of the valve from the holder member. A similar groove runs around the outer surface of the opposing finger 12. The finger 12 is somewhat narrower than finger 11 and has a central slot 14 adapted to slip over the strut of the heart valve.

Figure 6:
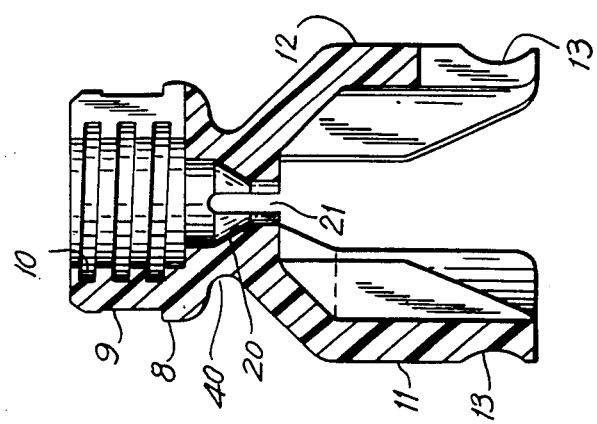
FIG. 6 is a cross-section through the holder member.
Figure 5:
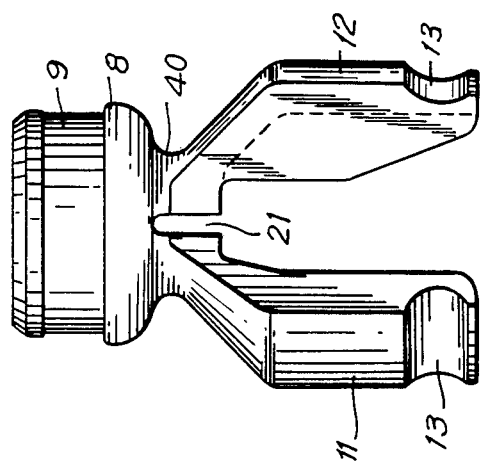
FIG. 5 is another side elevation of the holder member.
Figure 4:
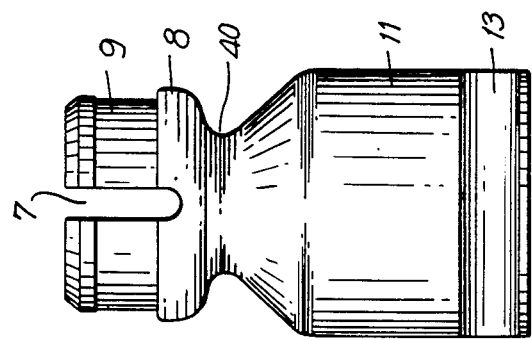
FIG. 4 is an enlarged side elevation of holder member.

The elements of the holder member are illustrated in greater detail in FIGS. 4, 5 and 6.

Figure 7:
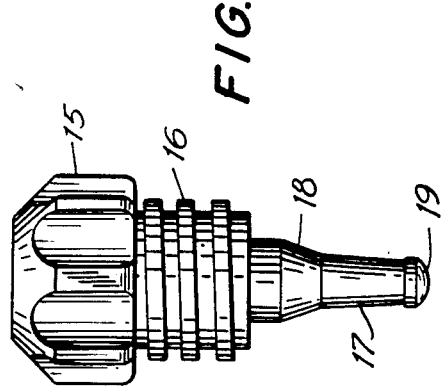
FIG. 7 is an enlarged side elevation of the engaging screw.
Figure 8:
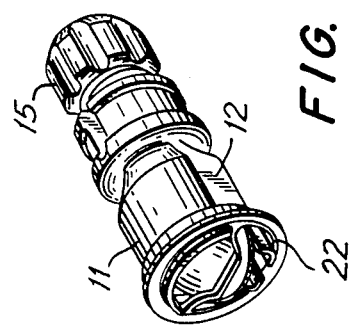
FIG. 8 is a perspective view of the holder member holding a prosthetic aortic monostrut valve.
Figure 10:
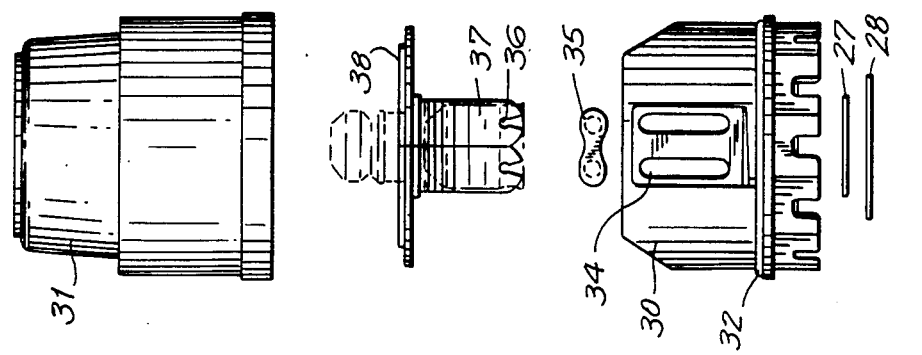
FIG. 10 is a side elevation of the separated parts of the inner container of the assembly of FIG. 9.
Figure 9:
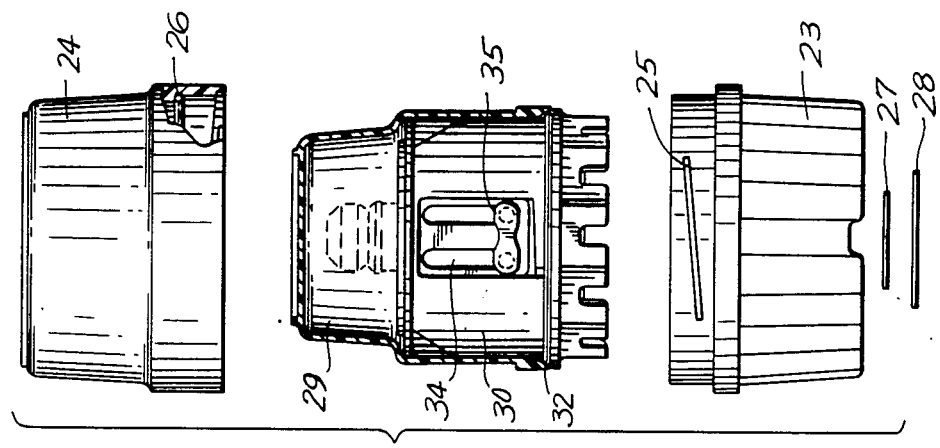
FIG. 9 is a side elevation of the separated parts of a preferred package assembly.
Figure 11:
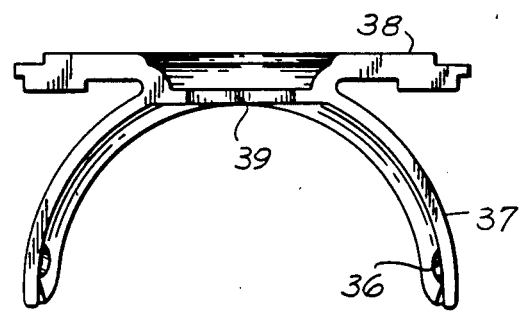
FIG. 11 is an end elevation of one half of the split platform.
Figure 12:
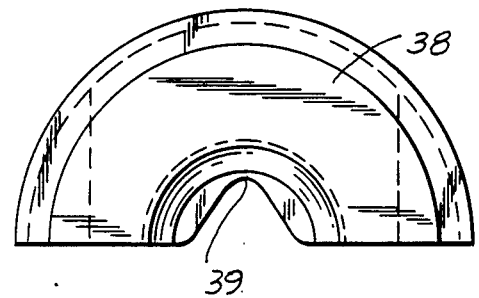
FIG. 12 is a plan view of one half of the split platform.

FIG. 7 illustrates the engaging screw which interacts with the holder member (see FIG. 6) to control and limit the movement of the fingers. The engaging screw comprises a turning knob 15, a threaded body 16 which screws into the screw thread 10 and a projecting spigot 17 having a tapered wedge 18 near its proximal end and convex knob 19 at its distal end. When the screw is tightened the wedge 18 bears against the tapered inner wall 20 (FIG. 6) of the holder member forcing the fingers outwardly about the pivotal slot 21. The outward movement of the fingers tightens them against the ring of the heart valve 22, as shown in FIG. 8, thereby holding the valve by the holder member. An important feature of this embodiment is that the configuration of the screw and spigot is such that the outward movement of the fingers is controlled and limited. The limit to the outward movement of the fingers prevents excessive radial forces being applied to the ring of the valve and thus prevents damage to the valve.

Loosening of the screw eases the pressure of the wedge against the inner wall of the holder member, allows the fingers to relax inwardly and thereby releases the valve from the holder member.

Preferably the engaging screw is made from black Delrin.

Figure 14:
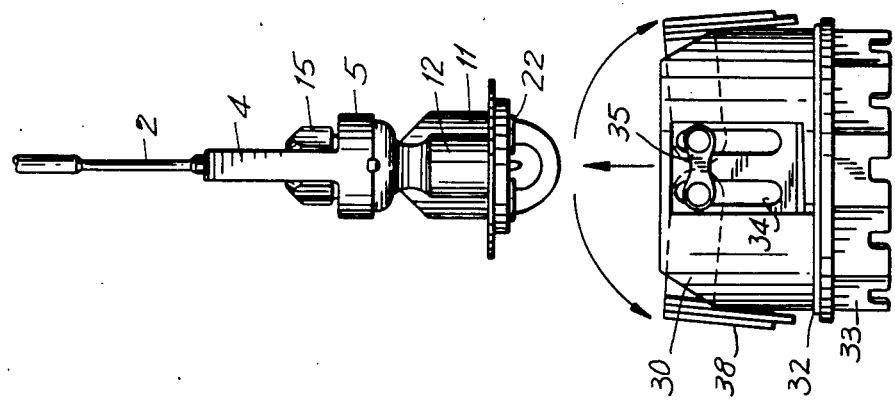
FIG. 14 is a side elevation of the housing showing the position of the said elements after release of the holder member and valve.
Figure 13:
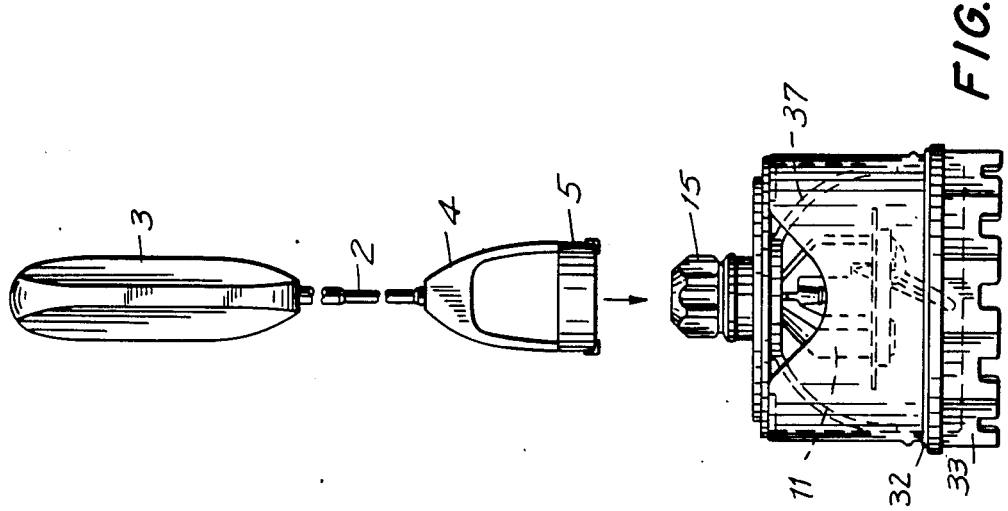
FIG. 13 is a side elevation of the housing showing the relative positions of the various elements before release of the holder member and attached valve.

FIGS. 9–12 illustrate the various parts of the preferred package assembly according to the invention, and FIGS. 13 and 14 illustrate the steps involved in removal of the holder member and valve from the package assembly.

The package assembly comprises an outer container having a bottom portion 23 and a tight fitting lid 24. To ensure a tight fit the lid screws on to the bottom portion about screw thread 25 and the lid is preferably provided with a sealing O-ring 26, preferably made of silicone.

If desired, the base of the bottom portion may have a circular hole into which is fitted a laminar air-gas filter 27 held in place by a filter support 28. Usually the filter is attached to the base of the housing.

Fitting within the outer container is an inner container 29, which comprises a housing 30 having a cover 31. When assembled together a tight fit between the cover and the housing is obtained with the aid of a silicone O-ring 32.

The housing preferably has a circular flat base with a castellated apron 33 which enables the base of the housing to stand proud from the base of the outer container.

In the embodiment illustrated the housing has a cylindrical vertical wall having a pair of slots 34 diametrically facing another pair of slots on the opposite side of the wall.

Each pair of slots carries a double pivoting fastener 35 which is adapted to slide up and down within said slots.

Each fastener is snap fitted into a keyhole slot 36 at the distal end of a downwardly extending limb 37. The proximal end of each limb is integrally attached to one half of a split platform 38. The split platform has a central hole 39 which is adapted to fit around the neck 40 of the holder member (see FIG. 6) for storage and shipment.

When each pivotal fastener is at its lowest point in each slot 34 the platform 38 rests on the upper edge of the cylindrical wall of the housing as shown in FIG. 13.

When the surgeon wishes to remove the valve from its sterile environment within the housing, the lid 24 is removed from the outer container and the inner container is taken out. The cover 31 is then removed from the housing and the key member, held by handle 3, is snapped into the holder member through slots 7.

Withdrawal of the handle, attached through the key member to the holder member and valve, lifts the valve from the housing and the two halves of the split platform 38 fall back over the sides of the housing as shown in FIG. 14. Upon release of the valve from the housing each pivotal fastener 35 is at the top of its associated slot 34 and each limb 37 is in a substantially horizontal position.

The combination of split platform, limbs, pivoting fasteners and slots as described above and illustrated in FIGS. 10-14 of the drawings forms a unique sliding mechanism herein designated as a "clam-shell" mechanism. An important feature of this mechanism is that the valve can not be released without a certain amount of force (using the handle and key member as described above) and therefore the valve can not accidentally fall out of the sterile container, for example if the container is inadvertently turned upside down.

All the various elements of the inner container and outer container of the package assembly, apart from the silicone O-rings and the optional air-gas filter, are made from a sterilizable plastic.

The package assembly and valve holder of the invention are particularly designed to allow the handle-containing member to be snapped into the holder member without the need for the surgeon to handle the valve itself. The valve is prepositioned on the holder member in the correct orientation for either aortic valve implantation which has the outflow portion of the disc (indented side) oriented toward the holder, or mitral valve implanting, which has the outflow portion of the disc (indented side) oriented away from the holder. Each holder device is clearly labelled for valve size, type, and orientation, i.e., aortic or mitral. Each device is designed to accept only the size, type and orientation of valve indicated on the device body.

The present invention thus provides a device which facilitates the holding and placement of a prosthetic heart valve; and a unique package assembly for storage and shipment of a valve under sterile conditions with simple and easy access when the valve is required.

We claim:

1. A device for releaseably holding an object which comprises:
    an elongated rod having a proximal end and a distal end,
    said rod being attached at its proximal end to a handle and at its distal end to a bifurcated member terminating in a ring enclosing a circular key member,
    a holder member readily attachable and detachable to said ring,
    said holder member terminating in at least two cooperating fingers and having a resilient cylindrical head with an axial screw thread, said fingers being adapted to engage with and grip an object to be held and said cylindrical head being adapted to be locked through a snapping engagement, within said circular key member, and
    an engaging screw located in said screw thread and adapted to interact with said holder member so as to control and limit the movement of said fingers and thereby, upon turning, to engage and disengage said fingers with respect to a desired object.

2. A device according to claim 1, in which said fingers are adapted to engage with and grip an annular heart valve ring from the inside and gripping is achieved by turning the engaging screw to expand the fingers outwardly.

3. A device according to claim 2, in which there are two fingers, each having the configuration of an arc of a circle and each being diametrically opposed to the other and each being provided with a shallow indent on the outer side near its distal end to accommodate the valve ring and prevent slipping when the engaging screw is tightened.

4. A method for releasably holding a prosthetic heart valve to facilitate placement or replacement thereof which comprises engaging the annular ring of said heart valve between the fingers of a device according to claim 2, turning the engaging screw of said device to expand said fingers and thereby grip and hold said heart valve.

5. A device according to claim 1, in which a portion of said elongated rod near its distal end is flexible.

6. A device according to claim 1, in which all the parts are made from sterilizable materials.

7. A device according to claim 5, in which the elongated rod and circular key member are made from stainless steel and the remaining parts are made from substantially rigid plastics material.

* * * * *